United States Patent [19]
Cochran et al.

[11] Patent Number: 4,972,093
[45] Date of Patent: Nov. 20, 1990

[54] INSPECTION LIGHTING SYSTEM

[75] Inventors: Don W. Cochran, Highland Heights; James R. Austin, Mentor-on-the-Lake, both of Ohio

[73] Assignee: Pressco Inc., Cleveland, Ohio

[21] Appl. No.: 439,553

[22] Filed: Nov. 20, 1989

Related U.S. Application Data

[63] Continuation of Ser. No. 336,642, Apr. 7, 1989, Pat. No. 4,882,498, which is a continuation of Ser. No. 107,265, Oct. 19, 1987, abandoned.

[51] Int. Cl.$^5$ ............................................. G01N 21/88
[52] U.S. Cl. ................................. 250/572; 250/223 R
[58] Field of Search ............... 250/562, 563, 571, 572, 250/223 R, 205; 313/500; 262/249, 252

[56] References Cited

U.S. PATENT DOCUMENTS

| | | | |
|---|---|---|---|
| 3,222,524 | 12/1965 | Lee | 250/106 |
| 4,141,566 | 11/1983 | Peyton et al. | 358/101 |
| 4,165,277 | 8/1979 | Frewin | 209/3.3 |
| 4,217,491 | 8/1980 | Dufford, Jr. et al. | 250/223 R |
| 4,271,408 | 6/1981 | Teshima et al. | 340/702 |
| 4,293,219 | 10/1981 | Ducloux | 356/240 |
| 4,305,658 | 12/1981 | Yoshida | 356/23 |
| 4,344,146 | 8/1982 | Davis, Jr. et al. | 364/522 |
| 4,364,088 | 12/1982 | Kubota | 358/106 |
| 4,367,405 | 1/1983 | Ford | 250/223 |
| 4,379,233 | 4/1983 | Rosenthal | 250/223 R |
| 4,380,025 | 4/1983 | Deane | 358/106 |
| 4,385,233 | 5/1983 | Lovalenti | 250/223 |
| 4,385,318 | 5/1983 | Miller | 358/106 |
| 4,427,880 | 1/1984 | Kanade et al. | 250/222.1 |
| 4,442,455 | 4/1984 | Huignard et al. | 358/209 |
| 4,446,481 | 5/1984 | Edamatsu et al. | 358/106 |
| 4,486,776 | 12/1984 | Yoshida | 358/106 |
| 4,491,868 | 1/1985 | Berridge, Jr. et al. | 358/139 |
| 4,509,076 | 4/1985 | Yoshida | 358/106 |
| 4,513,441 | 4/1985 | Henshaw | 250/562 |

(List continued on next page.)

FOREIGN PATENT DOCUMENTS

| | | |
|---|---|---|
| 341806 | 2/1989 | European Pat. Off. |
| 336563 | 3/1989 | European Pat. Off. |

OTHER PUBLICATIONS

A. Novini, "Fundamentals of Machine Vision Lighting", Penn Video Inc., Copyright 1985.
Penn Video Inc., "Pulsar Machine Vision Strobes".
A. Novini, "Fundamentals of Strobe Lighting for Machine Vision", Penn Video Inc., Copyright 1987.
G. Wagner, "Combining X-Ray Imaging and Machine Vision", Penn Video Inc., Copyright 1987.
A. Novini, "Fundamentals of Machine Vision Component Selection", Penn Video Inc., Copyright 1984.
Penn Video Inc., "Programmable Logic Controlled Vision".
SME Manufacturing Engineering, Manufacturing Insights: The Video Tape Series for Industrial Management, "Machine Vision, Trends in Technology", Copr. 1985.
Schreiber, Rita R., Quality Control with Vision, Vision MVA/SME's Quarterly on Vision Technology, vol. 2, No. 4 (Oct., 1985).
George, Robert W., High Speed Video Inspection of Caps and Closures, Vision '85 Conference Proceedings, pp. 1-55 through 1-70 (Mar. 25-28, 1985).
Vinarub, E. J. et al., Fiber Optics in Machine Vision, Photonics Spectra, (Jun. 1987).

*Primary Examiner*—David C. Nelms
*Assistant Examiner*—Khaled Shami
*Attorney, Agent, or Firm*—Fay, Sharpe, Beall, Fagan, Minnich & McKee

[57] ABSTRACT

An engineered lighting system for use in an inspection system is comprised of an array of light emitting diodes. A specimen is brought into the viewing area, and a current pulse is provided to the diodes of the array to selectively flash all or a portion of the diodes of the array. Reflected light from the specimen is sensed and a digitized image is generated therefrom. An illumination level of the digitized image is adjustable, in whole or in part, by varying the effective lighting intensity of one or more of the diodes of the array during a flash period. The digitized image of the specimen is compared to data indicative of acceptability of the specimen, and acceptance or rejection of the specimen is decided on a basis of a comparison therebetween.

34 Claims, 8 Drawing Sheets

U.S. PATENT DOCUMENTS

| | | | |
|---|---|---|---|
| 4,530,036 | 7/1985 | Conti | 362/32 |
| 4,567,551 | 1/1986 | Choate | 362/398 |
| 4,581,632 | 4/1986 | Davis et al. | 358/106 |
| 4,595,289 | 6/1986 | Feldman et al. | 356/237 |
| 4,604,648 | 8/1986 | Kley | 358/101 |
| 4,606,635 | 6/1986 | Miyazawa et al. | 356/240 |
| 4,677,473 | 6/1987 | Okamoto | 358/101 |
| 4,699,273 | 10/1987 | Suggi-Liverani et al. | 250/223 R |
| 4,731,649 | 3/1988 | Chang et al. | 358/106 |
| 4,758,084 | 7/1988 | Tokumi et al. | 356/237 |
| 4,764,681 | 8/1988 | Michaiski et al. | 250/563 |
| 4,811,251 | 3/1989 | Minato | 364/552 |
| 4,843,231 | 6/1989 | Caloyannis et al. | 250/223 B |
| 4,865,447 | 9/1989 | Shay | 356/240 |

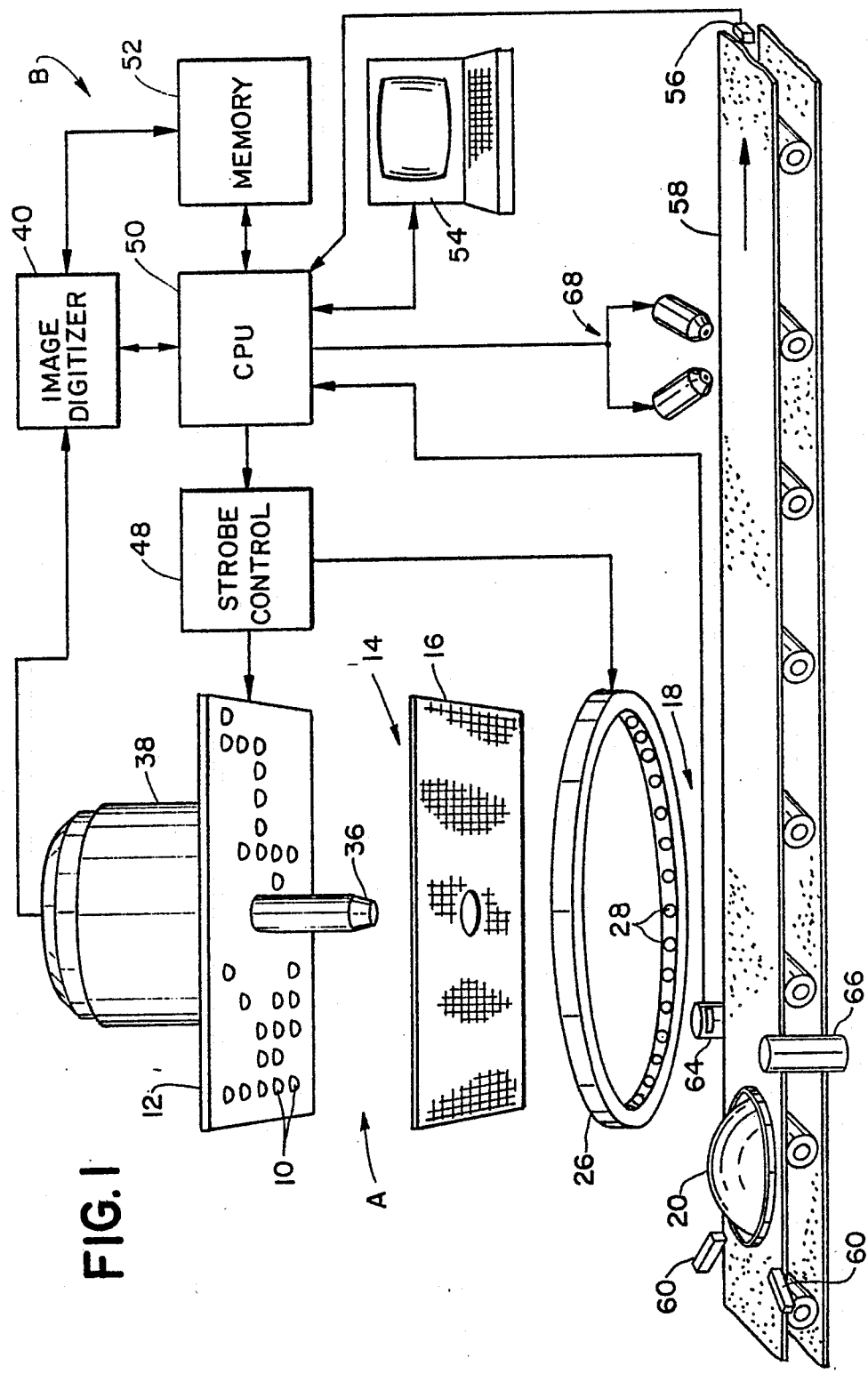

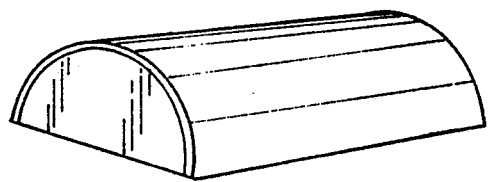
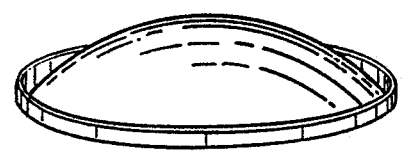
FIG. 2A    FIG. 2B
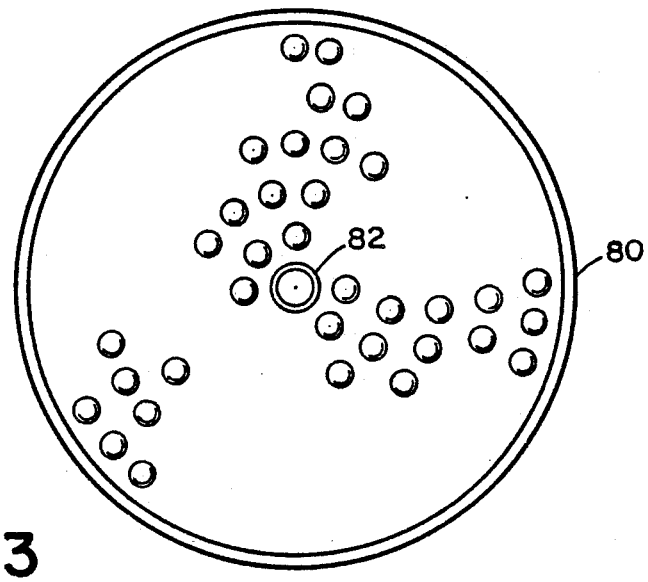
FIG. 3
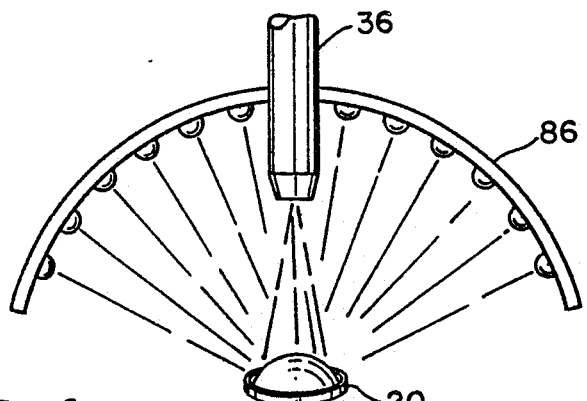
FIG. 4

INSPECTION LIGHTING SYSTEM

This application is a continuation of co-pending U.S. patent application Ser. No. 336,642, filed Apr. 7, 1989, which has been assigned U.S. Pat. No. 4,882,498 issuing on Nov. 21, 1989, which application is, in turn, a file-wrapper continuation of U.S. patent application Ser. No. 107,265, filed Oct. 19, 1987 and now abandoned.

BACKGROUND OF THE INVENTION

This application pertains to the art of engineered lighting systems, and more particularly to engineered lighting systems for lighting of specimens in an inspection environment.

The invention is particularly applicable to video inspection apparatuses and will be described with particular reference thereto, although it will be appreciated that the invention has broader applications such as lighting of specimens in any inspection or computer vision system.

Machine vision systems are obtaining increasing significance in industry to aid in robotic assembly systems as well as inspection systems for quality control. Such machine vision systems are generally comprised of a lighting system to light a specimen and a camera for sensing light reflected therefrom. A digitized image is formed from an image received by the camera. The data of this image is then available for use in controlling a robot arm, indentifying the specimen, or determining whether the specimen is acceptable to specified standards. The ability to govern operations in accordance with an inspected specimen is dictated by the quality of the digitized image.

Early attempts on improving the accuracy of image data were directed to improvements in cameras and performance of algorithms on captured image data, in an effort to improve integrity, contrast, or resolution thereof. Little emphasis was placed on the lighting systems, which, in a typical video inspection system, were comprised of inert gas strobe lamps, such as xenon strobes, particularly when specimens are in motion relative to the video camera. For non-moving specimens, common steady-state light sources such as fluorescent, quartz-halogen, incandescent, or the like, are typically used.

Such video lighting systems are plagued by a variety of problems. Placement of a single lamp over a specimen which includes a reflective surface often causes an image of the strobe lamp itself to be transmitted to an inspection device. Strobe lamps were also relatively expensive, varied in intensity from flash to flash, and tended to degrade over a period of time, thereby resulting in lessened resolution of a resultant video image. In applications in which many hundreds or thousands of inspections per minute are required, in addition to poor lighting characteristics, the strobes also require regular replacement, which resulted in additional down time of the entire inspection apparatus.

The present invention contemplates a new and improved apparatus and method for lighting of a specimen in a video inspection environment which overcomes all the above-referred problems and others, and provides a video inspection lighting system with increased resolution and longevity.

SUMMARY OF THE INVENTION

In accordance with the present invention, there is provided an array of directed light emitting elements which are secured to direct light emitted therefrom to a light field.

In accordance with a more limited aspect of the present invention, a diffuser plate blends the light emitted from various elements of the array and thereby serves to form a light field having an increased uniformity of light intensity thereover.

In accordance with a more limited aspect of the invention, the light emitting elements are comprised of electric, solid state devices, such as LED's.

In accordance with a still more limited aspect of the invention, the array of LED's is shaped.

In accordance with another aspect of the present invention, a second array of light emitting elements is implemented to provide light to a specimen at a different angle to the specimen as compared to the light provided by the primary array.

In accordance with another aspect of the present invention, there is provided a method of lighting a specimen in an inspection environment which implements the above-structure.

In accordance with still another aspect of the present invention, effective intensities of various elements of the array may be selectively varied.

An advantage of the present system is that a lighting system is provided with increased resolution in a resultant image of an illuminated specimen.

Another advantage of the present invention is the provision of a configured lighting array which provides evenness-of-illumination; contrast over a viewed object's surface appear when light reflected therefrom is focused at a viewing location.

Another advantage of the present system is the provision of a lighting system with increased longevity of the lighting elements.

Yet another advantage of the present invention is the provision of a video inspection apparatus wherein increased accuracy and resolution of an inspection process may be realized inexpensively by selectively varying a lighting of a specimen to be inspected.

Still another advantage of the present invention is the provision of a system which provide both on-line and off-line adjustment of a lighting system scheme by selectively varying activation of elements of an array.

Further advantages will be apparent to those of ordinary skill in the art upon reading and understanding of the subject specification.

Brief Description of the Drawings

The invention may take physical form in certain parts and arrangements of parts, embodiments of which will described in detail in this specification and illustrated in the accompanying drawings which form a part hereof and wherein:

FIG. 1 is a diagram illustrating an embodiment of a video inspection system incorporating an engineered lighting system of the present invention;

FIG. 2 illustrates two sample specimens for which an engineered lighting system of the present invention is well suited;

FIG. 3 is an alternate lighting array of the system of FIG. 1;

FIG. 4 is yet another alternative array of lighting elements of the system of FIG. 1;

DETAILED DESCRIPTION OF THE PREFERRED EMBODIMENTS

Figure 5A:
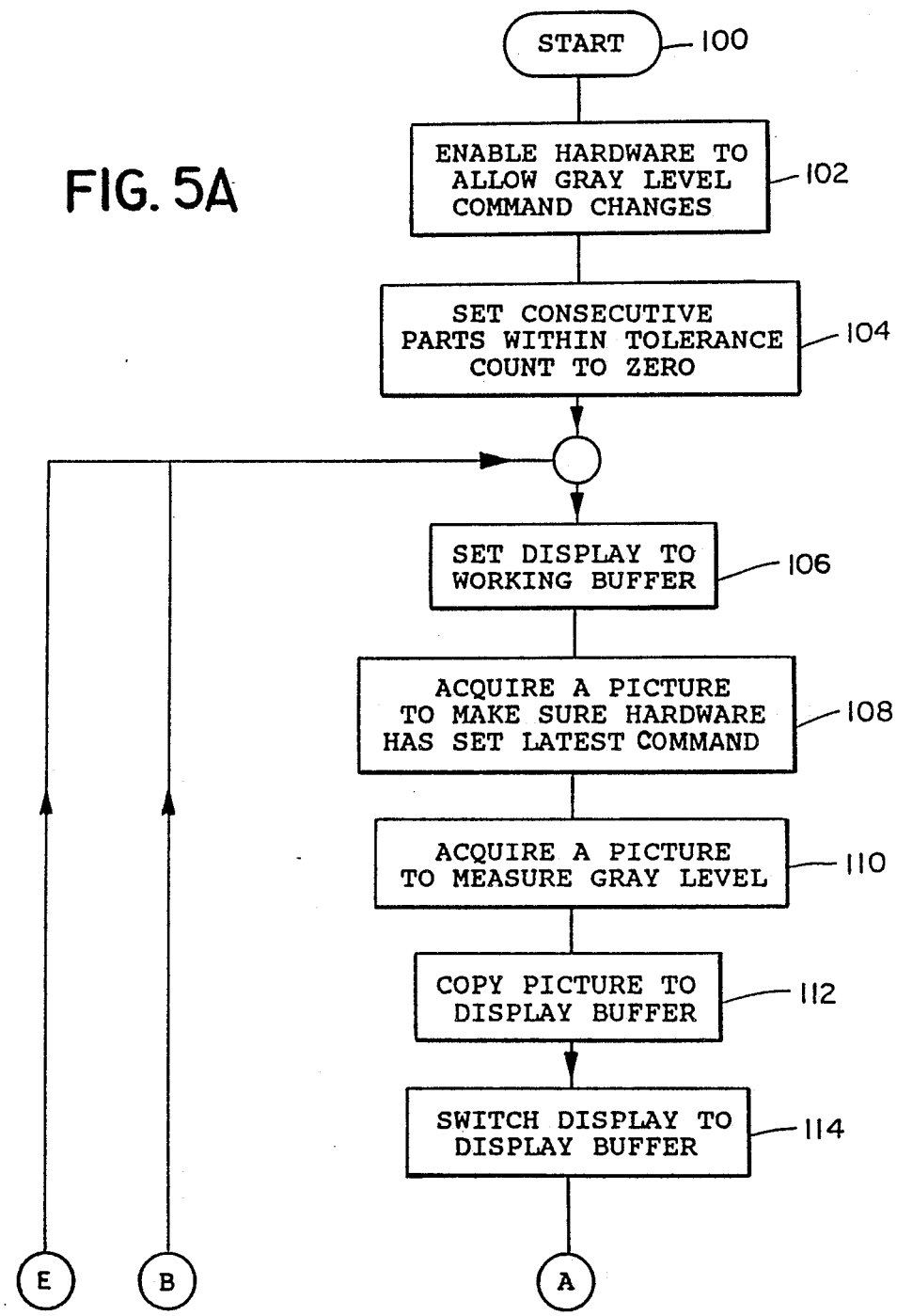
FIG. 5 (5a-5c) is a flow chart of gray scale calibration for off-line calibration of a video inspection system of the type of FIG. 1.

Referring now to the drawings, wherein the showing are for the purpose of illustrating the preferred embodiment of the invention only and not for the purpose of limiting the same, FIG. 1 shows a video inspection system including an engineered lighting apparatus A which is controlled by and supplies video information to a processor means B.

The engineered lighting apparatus A is comprised of a plurality of light emitting elements 10 which are secured in an array by a securing means 12 to form a primary lighting array.

The light emitting elements 10 are directed by the securing means 12 to primary light field 14 in which not every element of the array contributes equally to each section thereof. A diffuser plate or means 16 is placed in the light field 14 to further diffuse light therefrom to create a viewing area 18 with an increased uniformity thereover.

For viewing certain specimens, such as the circular/domed specimen 20 illustrated in the figure, a secondary light source is advantageous for obtaining increased contrast and resolution of the specimen. A secondary light source 26 is illustrated as a ring array of secondary light emitting elements 28. The light therefrom is directed to the viewing area 18 at an angle of travel thereto different from that of the primary array of elements 10. As illustrated, the light from the secondary array propagates such that a component of direction of travel of light therefrom is parallel to the plane of the primary array. This is particularly suited for the illustrated specimen 20 as it provides for side lighting at an angle perpendicular to the direction of travel from that the primary array of elements 10.

As illustrated, the elements 10 of the primary array create a diffused lighting for a specimen by means of the diffuser 16. Specular (non-diffused), directly reflected light, is resultant on the specimen by the array of secondary light emitting elements 28. It will be appreciated, however, that either diffused or specular lighting from either array is desirable or satisfactory in applications dependent on the object to be viewed and the individual properties thereof. The preferred embodiment is, however, as illustrated in FIG. 1.

Both the primary light emitting elements 10 and the secondary light elements 28 are preferably comprised of electrically powered solid state lighting devices, such as light emitting diodes ("LED's"), or the like. Focused LED's are preferred as they provide for selective illumination of a controlled portion of the viewing area 18. While it is difficult to obtain light of a suitable intensity from standard electronic lighting elements driven within their recommended current and voltage levels, in the video inspection environment, only a short viewing time is necessary. Accordingly, driving the solid state light element above its standard recommended ratings, for a relatively short duration, is found to provide suitable illumination without adversely affecting it. For example, a LED device overdriven for a duration in the range of 20-200 microseconds provides adequate illumination for a sufficient period with virtually no degradation of the element.

Although lighting of specimens for analysis in accordance with the present invention may be facilitated with light of one or more wavelengths, not limited to those of the visual spectrum, it has been found that suitable analysis is generally found with light of generally a single wavelength. As will be seen below, analysis of a specimen is ultimately facilitated on analysis of gray scale levels of black and white images, which may suitably be generated by LED's of a single color. For example, a commonly used red LED is generally adequate in many applications.

Light of any particular wave length may be obtained by use of appropriate light emitting elements. For example, ultraviolet or infrared light emitting diodes may be easily implemented. Combinations of two or more types of LED's may be made to provide for a viewing area comprising light from multiple frequencies or wavelengths. A combination such as red, green, and blue may be implemented to provide wave lengths of the entire visible spectrum, or any subcombination thereof.

When lighting of viewing area 18 is initiated, light thereof is reflected off of a specimen, located therein, to a monitor means 36. As illustrated, the monitor means 36 is comprised of a lens of a video camera means 38, from which an electronic signal representative of the specimen is obtained from the reflected light. The electronic image signal is transmitted to an image digitizer 40 wherein a numeric representation of the image is obtained by means of the familiar bit mapped technique. A numeric representation, such as a binary number, of a gray scale is accordingly assigned to a representation of each of a plurality of picture elements ("pixels") of a raster scan of the image. For each pixel, gray scale information is stored in a memory location for future retrieval and comparison.

Triggering or firing of the light emitting elements is selectively facilitated by means of a supply of one or more current pulses initiated from a strobe control means 48, which is in turn controlled by central processor unit ("CPU") 50.

The CPU 50 is suitably comprised of a digital computer which operates on a stored program located in memory 52 which is preferably random access memory (RAM). The memory 52 is also segmented into a working buffer region into which data onto which operations are performed, as well as a display buffer region which provides image data to an input/output (I/O unit) 54, in a standard bit-mapped graphics fashion, or the like. Both the working buffer and the display buffer are thereby adapted to store image data.

Also stored in memory 52 is a digital representation of a preselected image range against which specimen image data may be compared to determine whether a particular specimen is acceptable. As will be seen below, this data is both setable and alterable.

The CPU 50, in operation under a suitable software routine in the memory 52, facilitates comparison of the preselected image range data to that data indicative of an examined specimen. By suitable comparison in the CPU 50, a determination of acceptability of the subject specimen may be made. The CPU 50 also interfaces with the (I/O) unit 54. The I/O unit 54 permits display of digitized image data, display of an illuminated specimen, control of operation of the CPU 50, and modification of a software program in the memory 52.

Interfaced to the CPU 50 is a speed sensor 56 which provides a signal indicative of a velocity of a conveyor means 58 which is used to transport a series of specimens 20 to the viewing area 18. The specimens are centered in a selected orientation to the conveyor means 58 by a centering means 60.

The CPU 50 is also interfaced with a sensor means 64 which senses presence of a specimen 20 in the viewing area 18. As illustrated, the sensor means 64 is comprised of a photosensitive cell working in conjunction with a light emitter 66. A presence of a specimen in the viewing area results in a breakage of light path between the sensor 64 and the light emitter 66, thereby providing a signal indicative of an availability of the specimen for illumination and viewing.

When a specimen 20 has been viewed and digitized image resultant therefrom compared to preselected data parameters, acceptability of the subject specimen is determined by the CPU 50. A control signal is generated to facilitate rejection of an undesirable specimen by a rejecting means 68 which is illustrated as a plurality of air nozzles. The nozzles are oriented so as to remove a specimen 20 from the conveyor 58 by means of directed air streams.

A position of a specimen along the belt 58 is monitored to track the position of specimens therealong to facilitate removal by the means 68. The positioning may suitably be tracked by means of the speed sensor 56 working in conjunction with the sensor 64 by calculation of travel time from a triggering of the sensor 64 to the rejecting means 68. Of course, in such an arrangement, the speed sensor would be unnecessary should the conveyor be driven at a constant velocity by means such as a synchronous a.c. motor.

In operation, a series of specimens 20 travel along the conveyor 58. As each specimen enters the viewing area 18, a current pulse is provided under the direction of CPU 50 by strobe control 48, to selectively pulse the light emitting elements for a period suitable for obtaining a video image. Image data is captured through the monitor means 36 and the video camera means 38, and a digitized image thereof formed by the image digitizer 40. The image data is stored in memory 52, and compared with preselected data in CPU 50 to determine acceptability of the specimen by comparison thereof with preselected parameter data. This is accomplished by the CPU 50 acting in conjunction with a software routine in memory 52. Any non-conforming specimen is then rejected by provision of an air jet from the rejecting means 68.

Turning now to FIG. 2, three dimensional specimens for which video inspection by use of a lighting system as described above is particularly suited is illustrated. The objects illustrated include surfaces with directions that are not advantageously illuminated by a single light source. A mere planer array of light elements would not illuminate all surfaces evenly, as those surfaces which have a component of direction parallel to the direction of light propagation would thereby appear darker, with the darkness level being proportional to that component. In addition, absent a planar array of relatively uniform light, those surfaces of the specimen which are parallel to a single plane of light elements would present a reflection or image of the lighting element itself, and not a visual signal indicative of the properties of that surface which is as significant as is desirable.

The implementation of an LED array, as illustrated in FIG. 1, which acts in conjunction with a CPU control, is particularly suited for manipulations in lighting in accordance with a specimen under review. The CPU is suitably adapted for individual, or group, control of selected firing of various combinations or subcombinations of light emitting elements of the array. With such individual control, software modifications of a lighting system are made possible by selective control of which light emitting elements are activated at any particular time, and the extent to which they are activated. Such is suitably referred to as "dark field" illumination.

When the light emitting elements are comprised of LED's, an effective intensity of illumination therefrom may be varied not only with fluctuation of current levels at which the LED's are driven, but also by variations in the duration during which the LED remains on. As the LED's are comprised of those of the focused variety, a relatively small area of an illuminated specimen may be controlled by means of a small grouping in its elements of the array. When a camera is used to create a gray scale image, the brightness level sensed by the camera will be affected as a function of the duration at which the particular light sensitive elements therein are exposed to light. Accordingly, fluctuations in effective illumination levels of a particular portion of a specimen may be obtained by varying the time during which a corresponding LED is activated. It is found that a suitable gray scale adjustment is facilitated by varying the on time of the LED's from an on duration in the range of 20 microseconds to 200 microseconds. The actual on time of any LED or grouping thereof is controlled by means of the strobe control 48 working under direction of the CPU 50.

The ability to selectively vary the effective intensity of the LED's, in addition to facilitating viewing of non-uniform surfaces, provides means to allow for closed-loop correction of lighting patterns. Should one or more of the elements of the array degrade over time, the element may be controlled to compensate for this degradation. Also, should one element fail entirely, the effective illumination of its neighboring elements can be increased to compensate for its loss. Additionally, gradual variations in the specimens themselves which merits compensation in illumination levels is possible. Means for accomplishing such will be described further below.

In illuminating the specimens of FIG. 2, a gradual sloping of surfaces may be compensated for by increasing light from certain of light elements of a shaped (illustrated as planar) array, or alternatively, by triggering the elements of the secondary array.

Turning to FIG. 3, an alternate, circular array formed of lighting elements is provided which is suitable for illumination of a specimen such as that of FIG. 2B. To facilitate for illumination of such a specimen, the array may have more elements from a perimeter 80 activated. Alternatively, those elements may either be driven at a higher intensity level than those of the elements moving toward the center 82 of the array, or illuminated for a longer duration. Various lighting levels across a surface of a specimen may thereby be realized.

Turning to FIG. 4, another alternate array of lighting elements is provided which is particularly suited for viewing of a curved surface as illustrated by the specimens of FIG. 2. The curved array is shaped similarly to an exterior surface of the object to be viewed. A curved array 86 is provided, which preferably has a similar radius of curvature to that of the specimen. Such an array uses the property of light where an angle of incidence equals the angle of reflection. A yet more uniform gray scale pattern to view imperfections of the surface is provided when all lighting elements, have as a focus for reflected light, the monitor means 36.

As with the arrays described above, selected groups of light emitting elements from the array of FIG. 4 may similarly be enabled or varied, and the effective intensity thereby controlled to facilitate modifications in the lighting pattern via software control.

As noted above, the above-described system is particularly suited for the obtaining of a high resolution digitized image by means of an engineered lighting system. The present system is also designed to maintain consistency and quality of analysis by accounting for such factors as variations in lighting due to failure of individual lighting elements of an array, or degradation of lighting elements over an extended period of use. Illumination levels also vary due to factors such as metal characteristics and the like. Such may result in rejection of suitable specimens due to gradual trend toward variation from that which was previously within acceptable bounds. Accordingly, a continued updating and revision to gray scaled data is desirable. This may be accomplished either by manipulations of data in the CPU, or by variations in the lighting scheme of various subsets of elements of the lighting array as taught above.

Turning to FIG. 5, with reference again to FIG. 1, a flow chart is provided for a routine to be stored in memory 52 (FIG. 1) for operation of CPU 50 to facilitate variation in gray level readings from an analyzed specimen by varying the acceptable intensity levels realized from light emitting elements of the array.

The flow chart of FIG. 5 is directed to the off-line or set up gray level calibrations wherein an operator is permitted to view an image of a specimen during set-up, to initialize an illumination pattern thereof. The off-line set-up routine functions to perform analysis of a series of specimens and create an initial gray scale level therefrom. When a preselected number of consecutive specimens fall within gray scale bounds, the set-up is completed. When a variation is found, the gray scale is adjusted to account for the variation and the quest for the consecutive parts is recommenced. The particulars of this process are as discussed in the following routine.

With particular reference to FIG. 5a, a set-up operation is commenced at step 100, and hardware to allow changes of acceptable gray scale levels is enabled. As noted above, such variations in illumination may be accomplished by means of varying the on-time of one or more LED's of the array analogous the shutter speed control of a camera to vary exposure of various light sensitive elements of the video camera 38 to reflected light from a specimen 20.

Step 104 zeros a consecutive parts numbering counter which sets the number consecutive parts for which a conclusion of variation must be made to accomplish a gray scale adjustment. A display of the I/O unit 54 interfaced with a working buffer in the memory 52 in step 106. The LED array is pulsed and a picture is acquired from the camera 38 in step 108 A picture is again acquired in step 110, and the digitized image thereof is copied to a display buffer in step 112. The resultant image or picture date is then routed to the display at the I/O unit 54 from the display buffer, in step 114.

Figure 5B:
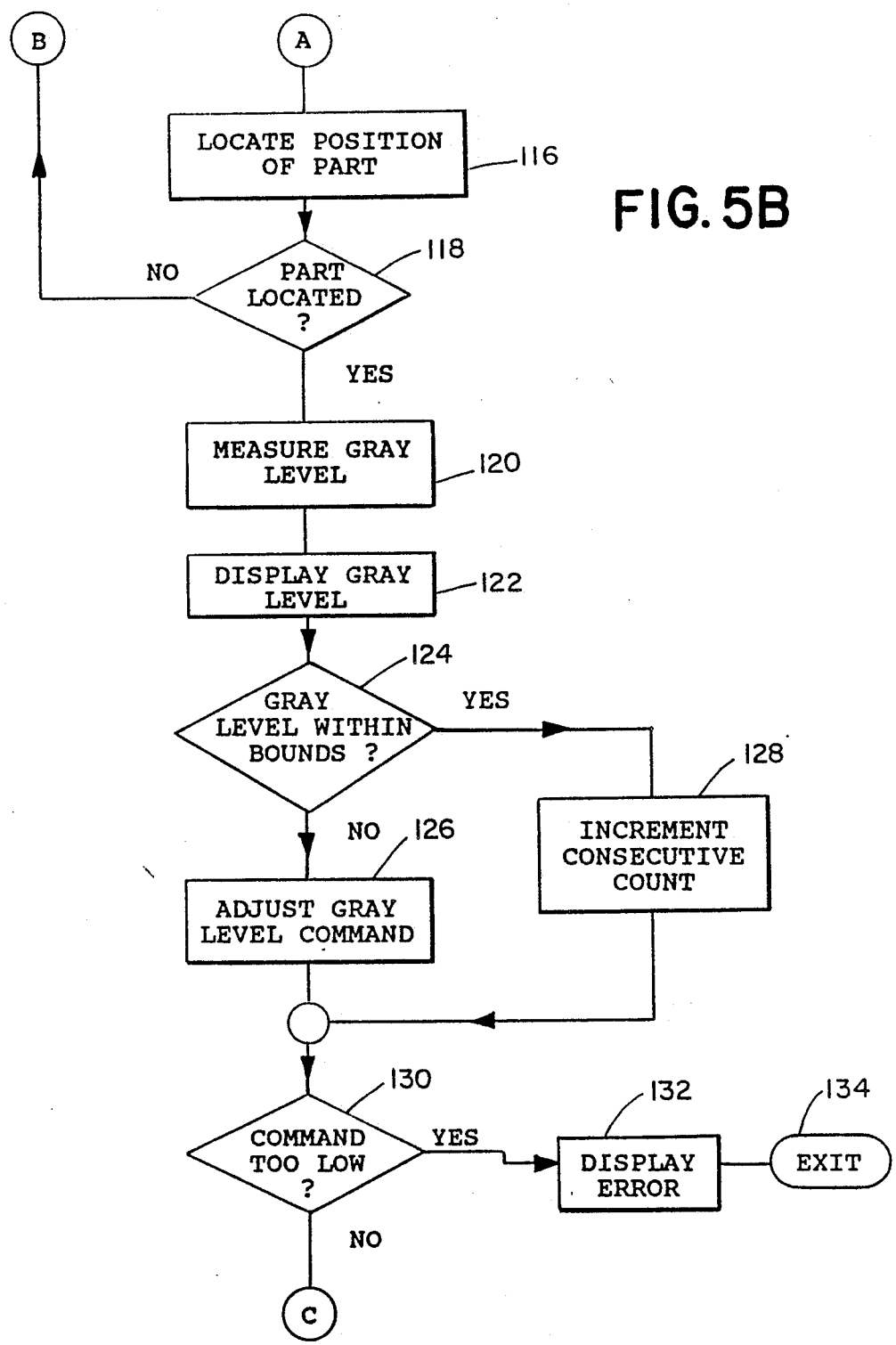

Turning particularly to FIG. 5b, as a specimen's position varies within the viewing area 18, in step 116 a position of a part or specimen is detected and fixed. After detection of such a part in step 118, a gray scale level is measured at step 120 and an image resultant therefrom is displayed at step 122. When a specimen is not located, the process returns to step 106 and proceeds therefrom. A test of this image data is made against selected parameters.

Figure 5C:
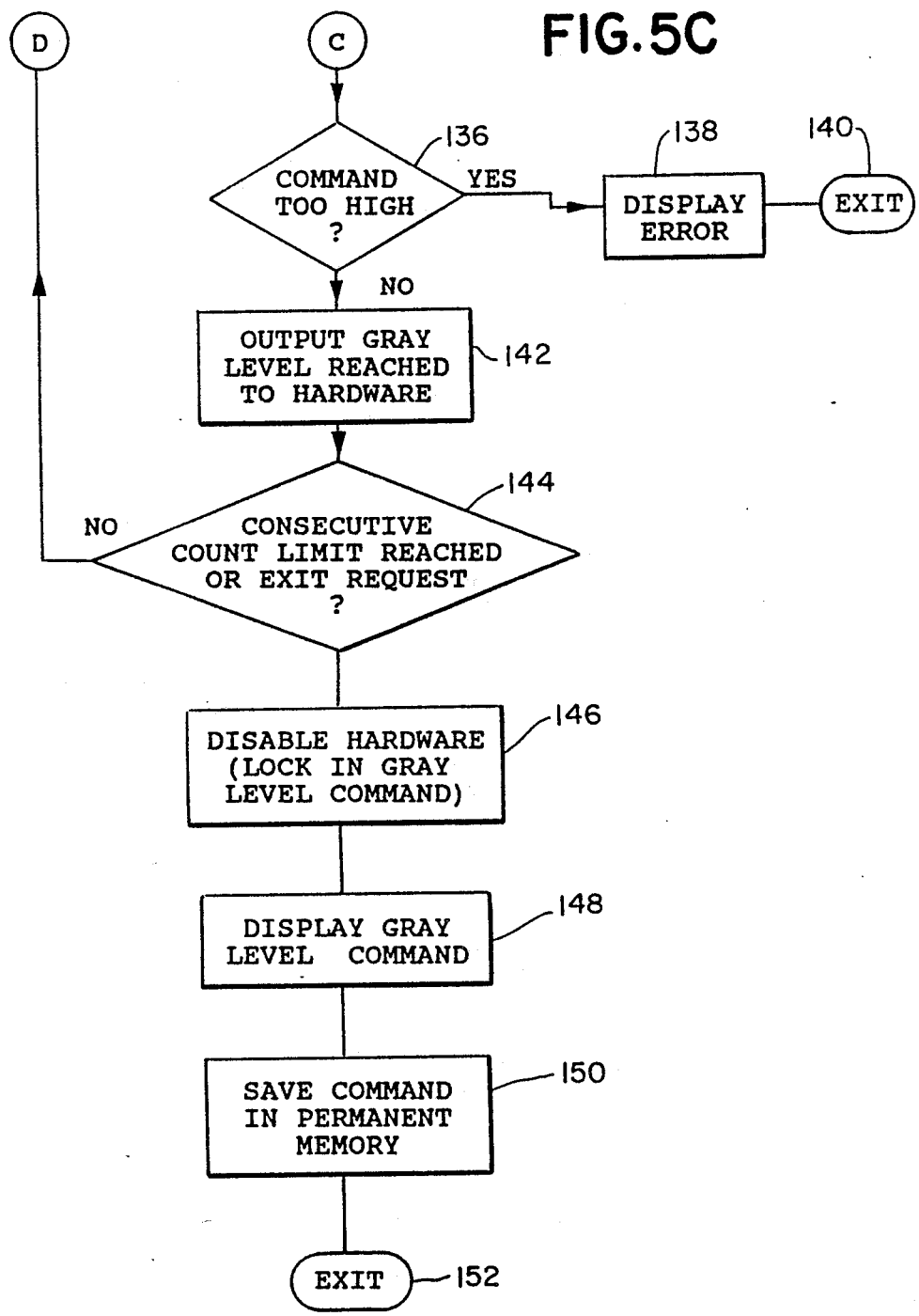

When the gray level is determined to be within the preselected bounds at step 124, the consecutive parts counter is incremented at step 128. When it is determined that the gray level is not within the preselected bounds, an adjustment thereof is made at 126. In either instance, the system proceeds to step 130 wherein the gray level command is tested to determine whether it is too low in accordance with a preselected standard. If it is too low, an error signal is generated at 132 and the process is aborted at 134. A negative determination at 130 allows for continuation of the process at 136 (FIG. 5c). At this step, it is determined whether the gray level command is too high, and if so, a corresponding error display is made at 130 and the system is exited at 140. If the gray level is acceptable, the system proceeds to step 142 wherein the gray level is set.

At step 144, the consecutive counter is tested to see whether the preselected number of consecutive parts fitting in the preselected gray level have been achieved. If not, the process is repeated from step 106 in a similar fashion as illustrated above.

Upon achieving a preselected number of consecutive parts within gray level parameters, the gray level adjustment hardware is disenabled at 146, the gray level command is displayed on the I/O unit 54 at 148, and the gray level is saved at step 150. At this time, the off-line gray scale adjustment is completed and the system is terminated at 152.

Figure 6A:
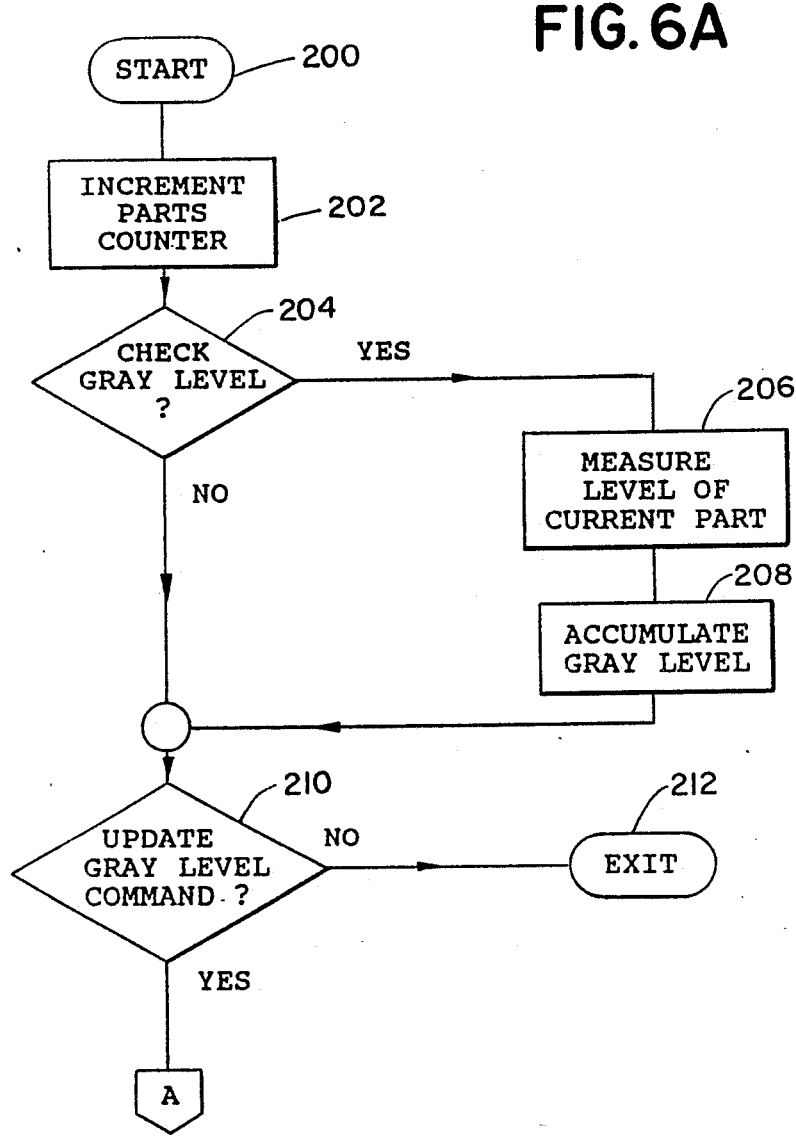
FIG. 6 (6a-6c) is a flow chart of gray scale calibration for on-line calibration of a video inspection system of the type of FIG. 1.

Turning to FIG. 6, with continued reference to FIG. 1, a flow chart for continuous adjustment of gray level which is performed during an actual production inspection (on-line) is disclosed. During testing of a plurality of specimens or parts, slight fluctuation trends in consecutive parts of an inspection run may be found due to variations in metal quality from separate batches, slight variations in coating thicknesses which are not sufficient to render a specimen unacceptable, or the like. Such variations may also result from degradation of lighting elements, or from a complete failure of one or more elements. The subject system provides for a closed loop feedback system which provides for continuous adjustment of the brightness level during such an inspection run. When a preselected number of consecutive parts provide a consistent variation in the gray scale level, a correction is made. Adjustment of the light intensity, for example by varying the duration during which the LED is illuminated, facilitates continuous refinement during an inspection run.

The on-line gray scale calibration is commenced at step 200, and a parts counter, which is initially zeroed, is incremented at step 202. When a part 20 enters the viewing area 18, the lighting array is triggered and a digitized video image is captured in memory 52. Determination of whether a gray level check is to be taken is made at step 204. An adjustment need not be made for each part in a series inspection. Selected or random checks may be instructed for this purpose. When a gray level check is to be made, a level measurement of a current part or specimen is made at step 206, and data indicative of the gray level of the subject specimen is obtained at 208. Determination of whether an updated gray level should be called for is made at step 210 and if not, the system is exited at 212.

Figure 6B:
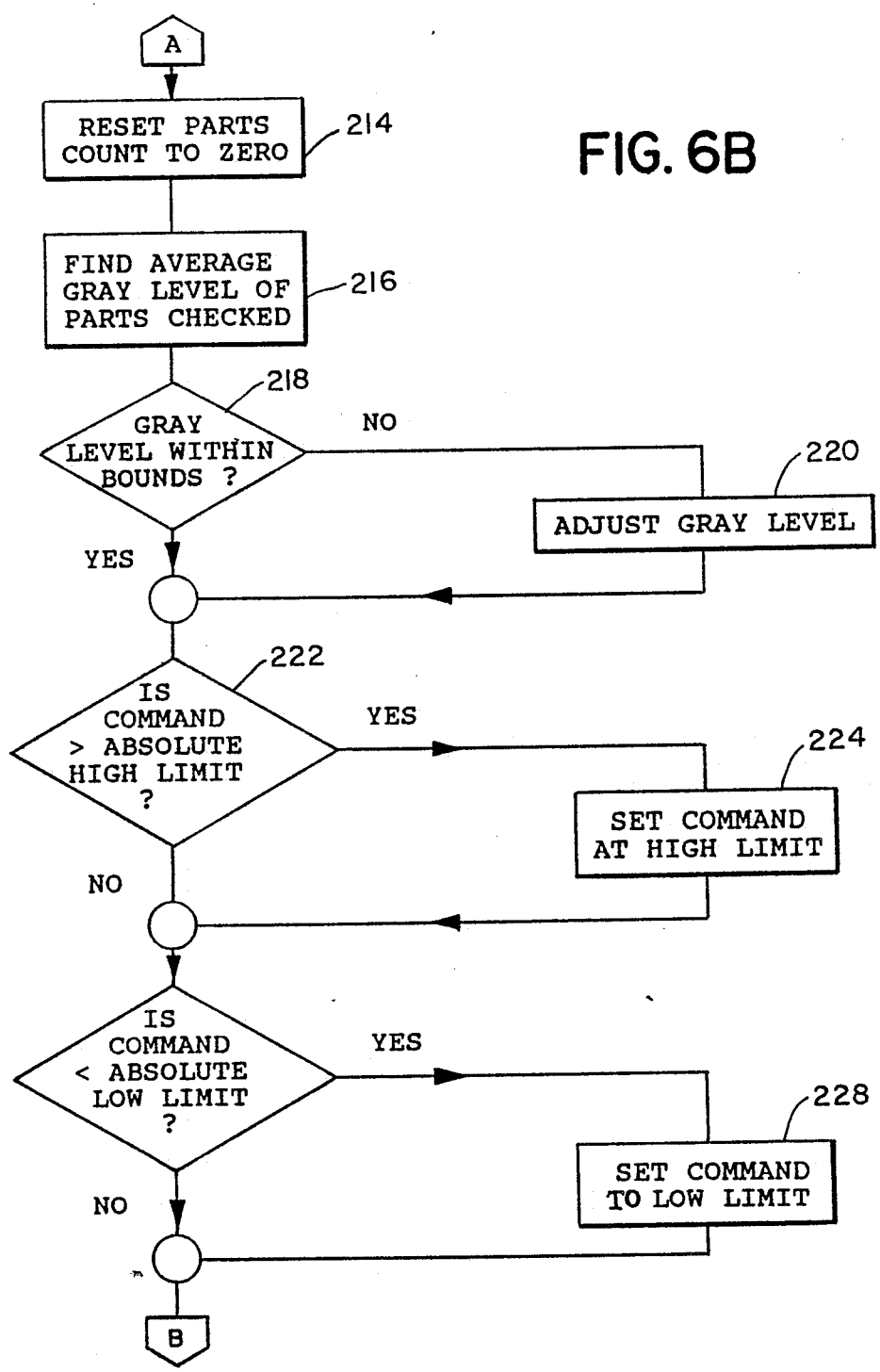

Proceeding to FIG. 6B, when it is determined that a gray level should be updated, the system proceeds to step 214 wherein a parts counter is reset to zero. An average gray level of checked parts is obtained at step 216. A determination is made at 218 whether the accumulated gray level is within preselected bounds. In either instance, a test is made at 222 to determine whether an absolute high limit of the gray scale has been exceeded. If so, the high level is readjusted at 224. In either instance, a similar check of the absolute low limit is made at 226 and readjusted is made when necessary at step 228.

Figure 6C:
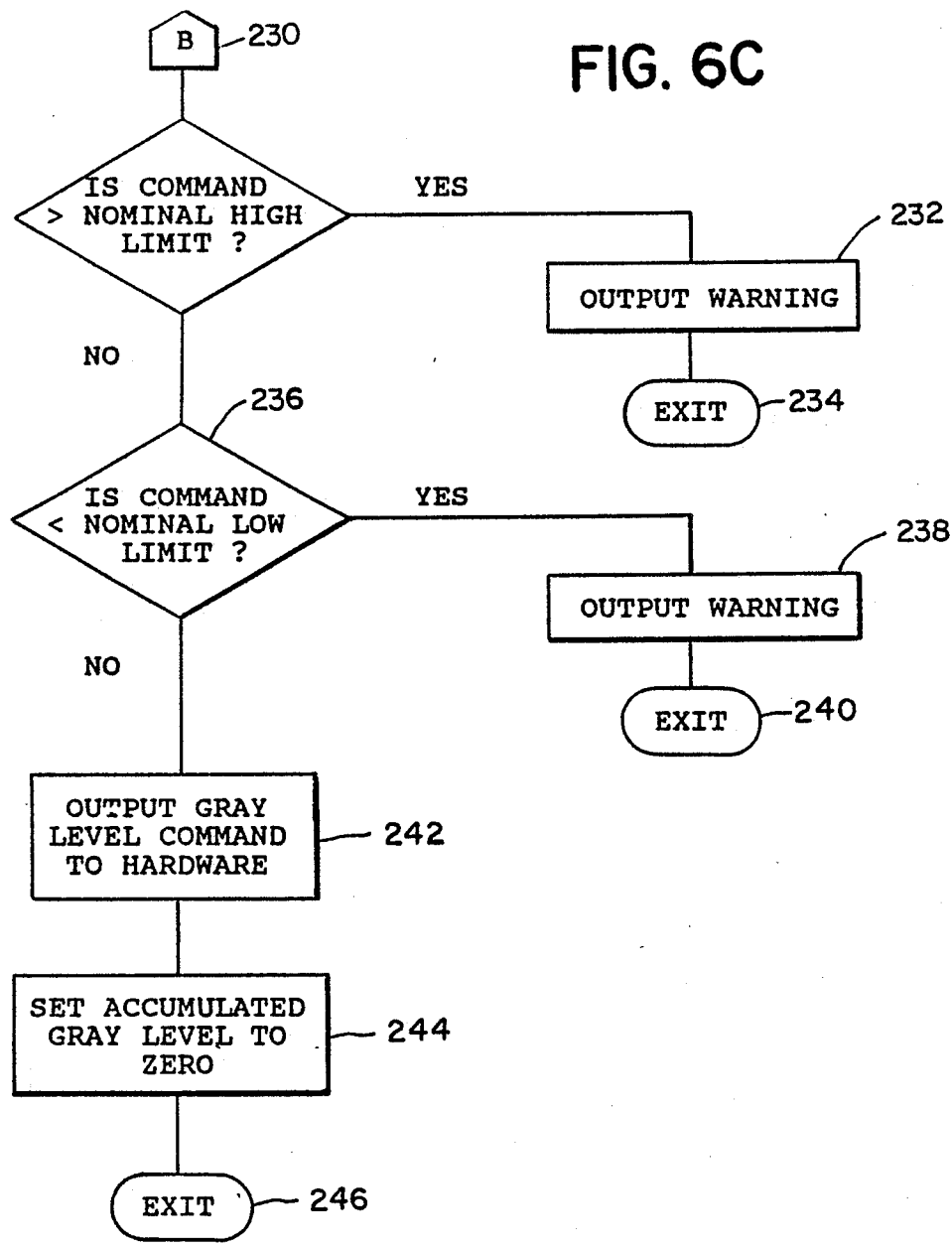

Turning to FIG. 6c, a determination is next made at step 230 whether the adjusted level has exceeded a preselected nominal high limit. If so, an output warning is given at 232 and the system terminated at 234 to allow for additional verification of whether the system is performing adequately. If the nominal high limit has not been exceeded, a similar test is made at step 236 with regard to a nominal low limit, with a similar output warning given at step 238, and an exit at 240 should this nominal low limit be exceeded. If both the nominal high limits and nominal low limit have not been exceeded, the system proceeds to step 242 wherein the modified gray level parameters are set. From this, modifications to the lighting to compensate for gray scale levels may be made. The accumulated gray level is then zeroed at step 244, and the on-line adjustment scheme exited at step 246.

The invention has been described with reference to the preferred embodiments. Obviously modifications and alterations will occur to others upon the reading and understanding of the specification. It is my intention to include all such modifications and alterations insofar as they come within the scope of the appended claims or their equivalents thereof.

It is now claimed:

1. An engineered inspection lighting system comprising:
   a plurality of directed lighting elements;
   securing means for securing the plurality of lighting elements to be directed to a light field;
   the securing means including means for securing the lighting elements in a preselected array arrangement to form a lighting array;
   means adapted for directing light from the lighting elements to the light field so as to light an associated specimen disposed therein substantially solely by specular illumination; and
   supply means for selectively providing current to lighting elements of the lighting array to provide a single illumination period to the associated specimen disposed in the light field.

2. An engineered inspection lighting system comprising:
   a plurality of directed lighting elements;
   means for securing the plurality of lighting elements to be directed to a light field;
   the securing means including means for securing the lighting elements in a preselected array arrangement to form a lighting array;
   means adapted for directing light from the lighting elements to the light field;
   supply means for selectively providing current to lighting elements of the lighting array to provide a single illumination period to an associated specimen disposed in the light field;
   light sensitive transducer means for generating an electrical signal in accordance with light exposed thereto;
   lens means for focusing light onto the light sensitive transducer means, which light was generated as a result of current provided to the selected lighting elements of the array by the supply means, after exposure thereof to the associated specimen;
   means for generating an image data signal representative of light focused onto the light sensitive transducer means by the lens means; and
   means for altering the supply means in accordance with the image data signal.

3. The engineered inspection lighting system of claim 2 wherein the means for altering the supply means includes means for varying at least one of activation, intensity, or duration of selected of the plurality of lighting elements.

4. The engineered inspection lighting system of claim 2 wherein the plurality of directed lighting elements include elements of each of a plurality of lighting spectra.

5. The engineered inspection lighting system of claim 2 further comprising means for generating specimen data representative of a physical characteristic of the associated specimen in accordance with the image data signal.

6. The engineered inspection lighting system of claim 5 further comprising means for testing the specimen data against data representative of a desired physical characteristic of the associated specimen.

7. The engineered inspection lighting system of claim 6 further comprising means for transporting the associated specimen to the viewing area.

8. An engineered video inspection system comprising:
   a plurality of directed lighting elements;
   means for securing the plurality of lighting elements to be directed to a light field;
   means for securing the lighting elements in a preselected array arrangement to form a lighting array;
   means adapted for directing light from the lighting elements to the light field;
   supply means for selectively providing current to lighting elements of the lighting array to provide a single illumination period to each of a series of associated specimens sequentially disposed in the light field;
   transducer means for generating an electrical signal in accordance with light exposed thereto;
   a lens means for focusing light onto the light sensitive transducer, which light was generated as a result of current provided to the selected lighting elements of the array by the supply means, after exposure thereof to each of the series of associated specimens;
   means for generating a series of image data signals, representative of light from each of the series of associated specimens, focused onto the light sensitive transducer by the lens means; and
   means for accumulating acceptability data representative of acceptability of future associated specimens from at least a portion of the series of image data signals.

9. The engineered video inspection system of claim 8 further comprising means for testing each image data signal against the acceptability data to determine acceptability of a specimen from which the image data signal was obtained.

10. The engineered video inspection system of claim 9 further comprising means for updating the acceptability data in accordance with selected image data signals generated from the series of associated specimens.

11. A method of automated video inspection comprising the steps of:
sequentially conveying a sequence of specimens to a light field;
sequentially activating a lighting array to provide a single illumination period for each of the sequence of specimens to the light field therewith;
focusing light on a light sensitive transducer after each exposure thereof to each of the sequence of specimens;
generating a sequence of image data signals corresponding to each of the sequence of specimens;
comparing each of image data signals to data representative of acceptability of specimens; and
selectively rejecting specimens in accordance with the step of comparing.

12. The method of claim 11 further comprising the step of generating the data representative of acceptability of specimens from selected of the sequence of image data signals.

13. The method of claim 11 wherein the step of sequentially activating a lighting array further includes the step of sequentially activating the lighting array comprised of solid state light generating elements.

14. The method of claim 13 wherein the step of sequentially activating a lighting array further includes the step of sequentially activating the lighting array comprised of light emitting diodes.

15. The method of claim 14 wherein the step of sequentially activating a lighting array further includes the step of sequentially activating the lighting array formed of at least one ring of light emitting diodes.

16. An apparatus adapted for automated video inspection with an associated lighting array comprising:
means for sequentially conveying a sequence of specimens to a light field;
means for sequentially activating a lighting array to provide a single illumination period for each of the sequence of specimens in the light field;
means for focusing light on a light sensitive transducer after each exposure thereof to each of the sequence of specimens;
means for generating a sequence of image data signals corresponding to each of the sequence of specimens;
means for comparing each of the image data signals to data representative of acceptability of specimens; and
means for selectively rejecting specimens in accordance with an output of the means for comparing each of the image data signals.

17. The apparatus of claim 16 further comprising means for generating the data representative of acceptability of specimens from selected of the sequence of image data signals.

18. The apparatus of claim 16 wherein the lighting array is formed of a plurality of solid state light generating elements.

19. The apparatus of claim 18 wherein the solid state light generating elements are comprised of light emitting diodes.

20. The apparatus of claim 19 further comprising securing means for securing selected light emitting diodes of the lighting array into at least one ring of light emitting diodes.

21. The apparatus of claim 20 wherein the securing means further includes means for aligning the selected light emitting diodes such that they generally circumscribe the light field.

22. The apparatus of claim 19 wherein the means for sequentially conveying includes means for conveying the sequence of specimens to the light field with a continuous motion relative to the light sensitive transducer.

23. The apparatus of claim 22 wherein the light sensitive transducer includes a single video camera.

24. An apparatus adapted for automated video inspection with an associated lighting array comprising:
means for sequentially conveying a sequence of specimens to a light field with a continuous relative motion between the sequence of specimens and a single video camera;
means for sequentially activating a lighting array comprised of a plurality of light emitting diodes to provide a single illumination period for each of the sequence of specimens in the light field;
means for focusing light from the lighting array on the single video camera after each exposure thereof to each of the sequence of specimens;
means for generating a sequence of image data signals corresponding to each of the sequence of specimens;
means for comparing each of the image data signals to data representative of acceptability of specimens; and
means for selectively rejecting specimens in accordance with an output of the means for comparing each of the image data signals;
wherein the lighting array includes a primary array portion of the plurality of light emitting diodes and a secondary array portion of the plurality of light emitting diodes, the primary and secondary array portions differing such that an angle of propagation of light from light emitting diodes of the primary array portion to the light field is different from an angle of propagation of light from elements of the secondary to the light field.

25. The apparatus of claim 24 wherein at least the primary array portion is generally planar, and wherein a component of direction of travel of light from the secondary light portion is parallel to the primary array portion.

26. The apparatus of claim 22 wherein the means for generating a sequence of image data signals includes means for isolating each image data signal of the sequence of image data signals in accordance with light provided by the single illumination period associated therewith, which single illumination period is obtained from activation of the lighting array by the means for sequentially activating.

27. The apparatus of claim 22 wherein:
the solid state light generating elements are further comprised of light emitting diodes particularly adapted for generating light in the visible spectrum; and
the means for sequentially activating includes overpulsing means for sequentially activating the lighting array such that the light emitting diodes thereof are driven above normal levels.

28. The apparatus of claim 27 wherein the overpulsing means includes means for pulsing the light emitting diodes for a duration in the range of 20 to 200 microseconds.

29. The apparatus of claim 24 further comprising securing means for securing selected light emitting diodes of the lighting array into at least one ring of light emitting diodes.

30. The apparatus of claim 29 wherein the securing means further includes means for aligning the selected light emitting diodes such that they generally circumscribe the light field.

31. The method of claim 14 further comprising the steps of conveying the sequence of specimens to the light field with a continuous motion relative to the light sensitive transducer.

32. The method of claim 31 wherein the step of focusing light includes the step of focusing the light on the light sensitive transducer formed as a single video camera.

33. The method of claim 31 further comprising the step of sequentially activating the lighting array such that the light emitting diodes thereof are driven above normal levels.

34. The method of claim 33 further comprising the step of pulsing the light emitting diodes for a duration in the range of 20 to 200 microseconds.

* * * * *